(12) United States Patent
Pal (10) Patent No.: US 7,850,708 B2
(45) Date of Patent: *Dec. 14, 2010

(54) EMBOLIC PROTECTION DEVICE HAVING A RETICULATED BODY WITH STAGGERED STRUTS

(75) Inventor: Dharmendra Pal, Wilmington, MA (US)

(73) Assignee: Cook Incorporated, Bloomington, IN (US)

( * ) Notice: Subject to any disclaimer, the term of this patent is extended or adjusted under 35 U.S.C. 154(b) by 734 days.

This patent is subject to a terminal disclaimer.

(21) Appl. No.: 11/455,471

(22) Filed: Jun. 19, 2006

(65) Prior Publication Data

US 2006/0287670 A1    Dec. 21, 2006

Related U.S. Application Data (60) Provisional application No. 60/692,313, filed on Jun. 20, 2005.

(51) Int. Cl.
*A61M 29/00*    (2006.01)
(52) U.S. Cl. .................... 606/200; 623/1.11; 623/23.72
(58) Field of Classification Search .............. 606/194, 606/200; 604/96.01; 623/1.11, 23.72
See application file for complete search history.

(56) References Cited

U.S. PATENT DOCUMENTS

| | | | |
|---|---|---|---|
| 3,547,103 A | 12/1970 | Cook |
| 3,635,223 A | 1/1972 | Klieman |
| 3,923,065 A | 12/1975 | Nozick et al. |
| 3,952,747 A | 4/1976 | Kimmell, Jr. |
| 3,978,863 A | 9/1976 | Fettel et al. |
| 3,996,938 A | 12/1976 | Clark, III |
| 4,425,908 A | 1/1984 | Simon |
| 4,494,531 A | 1/1985 | Gianturco |
| 4,548,206 A | 10/1985 | Osborne |
| 4,561,439 A | 12/1985 | Bishop et al. |
| 4,619,246 A | 10/1986 | Molgaard-Nielsen et al. |
| 4,643,184 A | 2/1987 | Mobin-Uddin |
| 4,646,736 A | 3/1987 | Auth |
| 4,650,472 A | 3/1987 | Bates |
| 4,665,906 A | 5/1987 | Jervis |
| 4,669,464 A | 6/1987 | Sulepov |

(Continued)

FOREIGN PATENT DOCUMENTS

WO    WO 96/10591    4/1996

(Continued)

*Primary Examiner*—Michael J Milano
*Assistant Examiner*—Victor X Nguyen
(74) *Attorney, Agent, or Firm*—Brinks Hofer Gilson & Lione (57) ABSTRACT

An embolic protection device for capturing emboli during treatment of a stenotic lesion in a body vessel is disclosed. The device comprises a basket and a filter attached to the basket. The basket has a deployed state and an undeployed state. The basket includes a reticulated body having an outer diameter. The reticulated body includes a plurality of struts connected together in a singly staggered configuration distally along a longitudinal axis to a distal end. The plurality of struts of the reticulated body is configured to fold along the longitudinal axis. The basket has a proximal stem proximally extending from the body. The filter portion has a lip attached to the distal end defining an opening of the filter portion when the basket is in the deployed state for capturing emboli. The filter portion extends from the lip to a filter end.

8 Claims, 4 Drawing Sheets

U.S. PATENT DOCUMENTS

| | | |
|---|---|---|
| 4,688,553 A | 8/1987 | Metals |
| 4,723,549 A | 2/1988 | Wholey et al. |
| 4,727,873 A | 3/1988 | Mobin-Uddin |
| 4,817,600 A | 4/1989 | Herms et al. |
| 4,824,435 A | 4/1989 | Giesy et al. |
| 4,832,055 A | 5/1989 | Palestrant |
| 4,873,978 A | 10/1989 | Ginsburg |
| 4,943,297 A | 7/1990 | Saveliev et al. |
| 4,957,501 A | 9/1990 | Lahille et al. |
| 4,990,156 A | 2/1991 | Lefebvre |
| 5,053,008 A | 10/1991 | Bajaj |
| 5,059,205 A | 10/1991 | El-Nounou et al. |
| 5,069,226 A | 12/1991 | Yamauchi et al. |
| 5,100,423 A | 3/1992 | Fearnot |
| 5,108,418 A | 4/1992 | Lefebvre |
| 5,108,419 A | 4/1992 | Reger et al. |
| 5,112,347 A | 5/1992 | Taheri |
| 5,129,890 A | 7/1992 | Bates et al. |
| 5,133,733 A | 7/1992 | Rasmussen et al. |
| 5,147,379 A | 9/1992 | Sabbaghian et al. |
| 5,152,777 A | 10/1992 | Goldberg |
| 5,160,342 A | 11/1992 | Reger |
| 5,234,458 A | 8/1993 | Metais |
| 5,242,462 A | 9/1993 | El-Nounou |
| 5,243,996 A | 9/1993 | Hall |
| 5,251,640 A | 10/1993 | Osborne |
| 5,263,964 A | 11/1993 | Purdy |
| 5,300,086 A | 4/1994 | Gory et al. |
| 5,324,304 A | 6/1994 | Rasmussen |
| 5,329,942 A | 7/1994 | Gunther et al. |
| 5,344,427 A | 9/1994 | Cottenceau et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,417,708 A | 5/1995 | Hall et al. |
| 5,527,338 A | 6/1996 | Purdy |
| 5,531,788 A | 7/1996 | Dibie et al. |
| 5,549,626 A | 8/1996 | Miller et al. |
| 5,562,698 A | 10/1996 | Parker |
| 5,601,595 A | 2/1997 | Smith |
| 5,624,461 A | 4/1997 | Mariant |
| 5,626,605 A | 5/1997 | Irie et al. |
| 5,634,942 A | 6/1997 | Chevillon et al. |
| 5,649,953 A | 7/1997 | Lefebvre |
| 5,669,933 A | 9/1997 | Simon et al. |
| 5,681,347 A | 10/1997 | Cathcart et al. |
| 5,690,667 A | 11/1997 | Gia |
| 5,693,067 A | 12/1997 | Purdy |
| 5,695,518 A | 12/1997 | Laerum |
| 5,695,519 A | 12/1997 | Summers et al. |
| 5,709,704 A | 1/1998 | Nott et al. |
| 5,713,853 A | 2/1998 | Clark et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,769,871 A | 6/1998 | Mers et al. |
| 5,795,322 A | 8/1998 | Boudewijn |
| 5,800,457 A | 9/1998 | Gelbfish et al. |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,830,230 A | 11/1998 | Berryman et al. |
| 5,836,968 A | 11/1998 | Simon et al. |
| 5,836,969 A | 11/1998 | Kim et al. |
| 5,846,260 A | 12/1998 | Maahs |
| 5,853,420 A | 12/1998 | Chevillon et al. |
| 5,876,367 A | 3/1999 | Kaganov et al. |
| 5,893,869 A | 4/1999 | Barnhart et al. |
| 5,895,391 A | 4/1999 | Farnholtz |
| 5,895,399 A | 4/1999 | Barbut et al. |
| 5,895,410 A | 4/1999 | Forber et al. |
| 5,908,435 A | 6/1999 | Samuels |
| 5,910,154 A | 6/1999 | Tsugita et al. |
| 5,911,704 A | 6/1999 | Humes |
| 5,911,717 A | 6/1999 | Jacobsen et al. |
| 5,911,734 A | 6/1999 | Tsugita et al. |
| 5,919,224 A | 7/1999 | Thompson et al. |
| 5,925,062 A | 7/1999 | Purdy |
| 5,925,063 A | 7/1999 | Khosravi |
| 5,928,260 A | 7/1999 | Chine et al. |
| 5,928,261 A | 7/1999 | Ruiz |
| 5,938,683 A | 8/1999 | Lefebvre |
| 5,941,896 A | 8/1999 | Kerr |
| 5,944,728 A | 8/1999 | Bates |
| 5,947,985 A | 9/1999 | Imran |
| 5,947,995 A | 9/1999 | Samuels |
| 5,948,017 A | 9/1999 | Taheri |
| 5,951,567 A | 9/1999 | Javier, Jr. et al. |
| 5,954,741 A | 9/1999 | Fox |
| 5,954,742 A | 9/1999 | Osypka |
| 5,954,745 A | 9/1999 | Gertler et al. |
| 5,968,057 A | 10/1999 | Taheri |
| 5,968,071 A | 10/1999 | Chevillon et al. |
| 5,972,019 A | 10/1999 | Engelson et al. |
| 5,976,162 A | 11/1999 | Doan et al. |
| 5,976,172 A | 11/1999 | Homsma et al. |
| 5,980,555 A | 11/1999 | Barbut et al. |
| 5,984,947 A | 11/1999 | Smith |
| 5,989,281 A | 11/1999 | Barbut et al. |
| 6,001,118 A | 12/1999 | Daniel et al. |
| 6,007,557 A | 12/1999 | Ambrisco et al. |
| 6,007,558 A | 12/1999 | Ravenscloth et al. |
| 6,010,522 A | 1/2000 | Barbut et al. |
| 6,013,093 A | 1/2000 | Nott et al. |
| 6,015,424 A | 1/2000 | Rosenbluth et al. |
| 6,027,520 A | 2/2000 | Tsugita et al. |
| 6,036,717 A | 3/2000 | Mers Kelly et al. |
| 6,036,720 A | 3/2000 | Abrams et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,745 A | 5/2000 | Gelbfish |
| 6,059,814 A | 5/2000 | Ladd |
| 6,063,113 A | 5/2000 | Kavteladze et al. |
| 6,066,158 A | 5/2000 | Engelson et al. |
| 6,068,645 A | 5/2000 | Tu |
| 6,074,357 A | 6/2000 | Kaganov et al. |
| 6,077,274 A | 6/2000 | Ouchi et al. |
| 6,080,178 A | 6/2000 | Meglin |
| 6,083,239 A | 7/2000 | Addis |
| 6,086,577 A | 7/2000 | Ken et al. |
| 6,086,605 A | 7/2000 | Barbut et al. |
| 6,093,199 A | 7/2000 | Brown et al. |
| 6,096,053 A | 8/2000 | Bates |
| 6,099,549 A | 8/2000 | Bosma et al. |
| 6,106,497 A | 8/2000 | Wang |
| 6,126,672 A | 10/2000 | Berryman et al. |
| 6,126,673 A | 10/2000 | Kim et al. |
| 6,129,739 A | 10/2000 | Khosravi |
| 6,136,016 A | 10/2000 | Barbut et al. |
| 6,146,396 A | 11/2000 | Konya et al. |
| 6,146,404 A | 11/2000 | Kim et al. |
| 6,152,931 A | 11/2000 | Nadal et al. |
| 6,152,946 A | 11/2000 | Broome et al. |
| 6,152,947 A | 11/2000 | Ambrisco et al. |
| 6,156,061 A | 12/2000 | Wallace et al. |
| 6,159,230 A | 12/2000 | Samuels |

| | | |
|---|---|---|
| 6,165,179 A | 12/2000 | Cathcart et al. |
| 6,165,198 A | 12/2000 | McGurk et al. |
| 6,165,199 A | 12/2000 | Barbut |
| 6,165,200 A | 12/2000 | Tsugita et al. |
| 6,168,579 B1 | 1/2001 | Tsugita et al. |
| 6,168,603 B1 | 1/2001 | Leslie et al. |
| 6,168,622 B1 | 1/2001 | Mazzocchi |
| 6,171,327 B1 | 1/2001 | Daniel et al. |
| 6,171,328 B1 | 1/2001 | Addis |
| 6,174,318 B1 | 1/2001 | Bates et al. |
| 6,179,851 B1 | 1/2001 | Barbut et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,193,739 B1 | 2/2001 | Chevillon et al. |
| 6,203,561 B1 | 3/2001 | Ramee et al. |
| 6,214,025 B1 | 4/2001 | Thistle et al. |
| 6,214,026 B1 | 4/2001 | Lepak et al. |
| 6,221,091 B1 | 4/2001 | Khosravi |
| 6,224,620 B1 | 5/2001 | Maahs |
| 6,231,588 B1 | 5/2001 | Zadno-Azizi |
| 6,231,589 B1 | 5/2001 | Wessman et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,550 B1 | 7/2001 | McNamara et al. |
| 6,254,633 B1 | 7/2001 | Pinchuk et al. |
| 6,258,026 B1 | 7/2001 | Ravenscroft et al. |
| 6,258,115 B1 | 7/2001 | Dubrul |
| 6,258,120 B1 | 7/2001 | McKenzie et al. |
| 6,261,305 B1 | 7/2001 | Marotta et al. |
| 6,264,672 B1 | 7/2001 | Fisher |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,277,125 B1 | 8/2001 | Barry et al. |
| 6,277,126 B1 | 8/2001 | Barry et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,287,321 B1 | 9/2001 | Jang |
| 6,290,710 B1 | 9/2001 | Cryer et al. |
| 6,306,163 B1 | 10/2001 | Fitz |
| 6,309,399 B1 | 10/2001 | Barbut et al. |
| 6,312,444 B1 | 11/2001 | Barbut |
| 6,319,268 B1 | 11/2001 | Ambrisco et al. |
| 6,325,815 B1 | 12/2001 | Kusleika et al. |
| 6,325,816 B1 | 12/2001 | Fulton, III et al. |
| 6,328,755 B1 | 12/2001 | Marshall |
| 6,331,183 B1 | 12/2001 | Suon |
| 6,331,184 B1 | 12/2001 | Abrams |
| 6,334,864 B1 | 1/2002 | Amplatz et al. |
| 6,336,934 B1 | 1/2002 | Gilson et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,048 B1 | 2/2002 | Chin et al. |
| 6,344,049 B1 | 2/2002 | Levinson et al. |
| 6,346,116 B1 | 2/2002 | Brooks et al. |
| 6,348,041 B1 | 2/2002 | Klint |
| 6,348,063 B1 | 2/2002 | Yassour et al. |
| 6,355,051 B1 | 3/2002 | Sisskind et al. |
| 6,358,228 B1 | 3/2002 | Tubman et al. |
| 6,361,545 B1 | 3/2002 | Macoviak et al. |
| 6,361,546 B1 | 3/2002 | Khosravi |
| 6,361,547 B1 | 3/2002 | Hieshima |
| 6,364,895 B1 | 4/2002 | Greenhalgh |
| 6,364,896 B1 | 4/2002 | Addis |
| 6,368,338 B1 | 4/2002 | Konya et al. |
| 6,371,969 B1 | 4/2002 | Tsugita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,379,374 B1 | 4/2002 | Hieshima et al. |
| 6,383,146 B1 | 5/2002 | Klint |
| 6,383,174 B1 | 5/2002 | Eder |
| 6,383,193 B1 | 5/2002 | Cathcart et al. |
| 6,383,196 B1 | 5/2002 | Leslie et al. |
| 6,383,205 B1 | 5/2002 | Samson et al. |
| 6,383,206 B1 | 5/2002 | Gillick et al. |
| 6,391,044 B1 | 5/2002 | Yadav et al. |
| 6,391,045 B1 | 5/2002 | Kim et al. |
| 6,395,014 B1 | 5/2002 | Macoviak et al. |
| 6,402,771 B1 * | 6/2002 | Palmer et al. ............... 606/200 |
| 6,402,772 B1 | 6/2002 | Amplatz et al. |
| 6,409,742 B1 | 6/2002 | Fulton, III et al. |
| 6,413,235 B1 | 7/2002 | Parodi |
| 6,416,530 B2 | 7/2002 | DeVries et al. |
| 6,419,686 B1 | 7/2002 | McLeod et al. |
| 6,423,086 B1 | 7/2002 | Barbut et al. |
| 6,425,909 B1 | 7/2002 | Dieck et al. |
| 6,428,557 B1 | 8/2002 | Hilaire |
| 6,428,558 B1 | 8/2002 | Jones et al. |
| 6,428,559 B1 | 8/2002 | Johnson |
| 6,432,122 B1 | 8/2002 | Gilson et al. |
| 6,436,112 B2 | 8/2002 | Wensel et al. |
| 6,436,120 B1 | 8/2002 | Meglin |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,447,531 B1 | 9/2002 | Amplatz |
| 6,458,139 B1 | 10/2002 | Palmer et al. |
| 6,458,145 B1 | 10/2002 | Ravenscroft et al. |
| 6,461,370 B1 | 10/2002 | Gray et al. |
| 6,468,290 B1 | 10/2002 | Weldon et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,500 B1 | 11/2002 | Kokish et al. |
| 6,485,501 B1 | 11/2002 | Green |
| 6,485,502 B2 | 11/2002 | Don Michael et al. |
| 6,491,712 B1 | 12/2002 | O'Connor |
| 6,494,895 B2 | 12/2002 | Addis |
| 6,497,709 B1 | 12/2002 | Heath |
| 6,499,487 B1 | 12/2002 | McKenzie et al. |
| 6,500,166 B1 | 12/2002 | Zadno Azizi et al. |
| 6,500,191 B2 | 12/2002 | Addis |
| 6,502,606 B2 | 1/2003 | Klint |
| 6,506,203 B1 | 1/2003 | Boyle et al. |
| 6,506,205 B2 | 1/2003 | Goldberg et al. |
| 6,508,826 B2 | 1/2003 | Murphy et al. |
| 6,511,492 B1 | 1/2003 | Rosenbluth et al. |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,527,962 B1 | 3/2003 | Nadal |
| 6,530,935 B2 | 3/2003 | Wensel et al. |
| 6,530,939 B1 | 3/2003 | Hopkins et al. |
| 6,530,940 B2 | 3/2003 | Fisher |
| 6,533,800 B1 | 3/2003 | Barbut |
| 6,537,293 B1 | 3/2003 | Berryman et al. |
| 6,537,294 B1 | 3/2003 | Boyle et al. |

| | | |
|---|---|---|
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,221 B1 | 4/2003 | Kokish et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,303 B1 | 4/2003 | Van Tassel et al. |
| 6,551,341 B2 | 4/2003 | Boylan et al. |
| 6,551,342 B1 * | 4/2003 | Shen et al. .................. 606/200 |
| 6,554,849 B1 | 4/2003 | Jones et al. |
| 6,558,404 B2 | 5/2003 | Tsukernik |
| 6,558,405 B1 | 5/2003 | McInnes |
| 6,558,406 B2 | 5/2003 | Okada |
| 6,562,058 B2 | 5/2003 | Seguin et al. |
| 6,565,591 B2 | 5/2003 | Brady et al. |
| 6,569,147 B1 | 5/2003 | Evans et al. |
| 6,569,183 B1 | 5/2003 | Kim et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,579,303 B2 | 6/2003 | Amplatz |
| 6,582,396 B1 | 6/2003 | Parodi |
| 6,582,447 B1 | 6/2003 | Patel et al. |
| 6,582,448 B1 | 6/2003 | Boyle et al. |
| 6,589,230 B2 | 7/2003 | Gia et al. |
| 6,589,263 B1 | 7/2003 | Hopkins et al. |
| 6,589,264 B1 | 7/2003 | Barbut et al. |
| 6,589,265 B1 | 7/2003 | Palmer et al. |
| 6,589,266 B2 | 7/2003 | Whitcher et al. |
| 6,592,546 B1 | 7/2003 | Barbut et al. |
| 6,592,606 B2 | 7/2003 | Huter et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,271 B2 | 8/2003 | Adams et al. |
| 6,602,273 B2 | 8/2003 | Marshall |
| 6,605,102 B1 | 8/2003 | Mazzocchi et al. |
| 6,607,506 B2 | 8/2003 | Kletschka |
| 6,610,077 B1 | 8/2003 | Hancock et al. |
| 6,613,074 B1 | 9/2003 | Mitelberg et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita |
| 6,620,182 B1 | 9/2003 | Khosravi et al. |
| 6,623,450 B1 | 9/2003 | Dutta |
| 6,623,506 B2 | 9/2003 | McGuckin, Jr. et al. |
| 6,629,953 B1 | 10/2003 | Boyd |
| 6,635,068 B1 | 10/2003 | Dubrul et al. |
| 6,635,069 B1 | 10/2003 | Teoh et al. |
| 6,635,070 B2 | 10/2003 | Leeflang et al. |
| 6,638,293 B1 | 10/2003 | Makower et al. |
| 6,638,294 B1 | 10/2003 | Palmer |
| 6,638,372 B1 | 10/2003 | Abrams et al. |
| 6,641,590 B1 | 11/2003 | Palmer et al. |
| 6,641,605 B1 | 11/2003 | Stergiopulos |
| 6,645,220 B1 | 11/2003 | Huter et al. |
| 6,645,221 B1 | 11/2003 | Richter |
| 6,645,222 B1 | 11/2003 | Parodi et al. |
| 6,645,223 B2 | 11/2003 | Boyle et al. |
| 6,645,224 B2 | 11/2003 | Gilson et al. |
| 6,652,554 B1 | 11/2003 | Wholey et al. |
| 6,652,557 B1 | 11/2003 | MacDonald |
| 6,652,558 B2 | 11/2003 | Patel et al. |
| 6,656,201 B2 | 12/2003 | Ferrera et al. |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,613 B1 | 12/2003 | Evans et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,695,865 B2 | 2/2004 | Boyle et al. |
| 6,702,834 B1 * | 3/2004 | Boylan et al. .................. 606/200 |
| 6,712,835 B2 | 3/2004 | Mazzocchi et al. |
| 6,726,701 B2 | 4/2004 | Gilson et al. |
| 6,758,855 B2 | 7/2004 | Fulton, III et al. |
| 6,761,727 B1 | 7/2004 | Ladd |
| 6,780,175 B1 | 8/2004 | Sachdeva et al. |
| 6,793,668 B1 | 9/2004 | Fisher |
| 6,866,677 B2 | 3/2005 | Douk et al. |
| 7,004,955 B2 * | 2/2006 | Shen et al. .................. 606/200 |
| 2001/0000799 A1 | 5/2001 | Wessman et al. |
| 2001/0001817 A1 | 5/2001 | Humes |
| 2001/0005789 A1 | 6/2001 | Root et al. |
| 2001/0007947 A1 | 7/2001 | Kanesaka |
| 2001/0011181 A1 | 8/2001 | DiMatteo |
| 2001/0011182 A1 | 8/2001 | Dubrul et al. |
| 2001/0012951 A1 | 8/2001 | Bates et al. |
| 2001/0016755 A1 | 8/2001 | Addis |
| 2001/0020175 A1 | 9/2001 | Yassour et al. |
| 2001/0023358 A1 | 9/2001 | Tsukernik |
| 2001/0025187 A1 | 9/2001 | Okada |
| 2001/0031980 A1 | 10/2001 | Wensel et al. |
| 2001/0031981 A1 | 10/2001 | Evans et al. |
| 2001/0031982 A1 | 10/2001 | Peterson et al. |
| 2001/0039431 A1 | 11/2001 | DeVries et al. |
| 2001/0039432 A1 | 11/2001 | Whitcher et al. |
| 2001/0041908 A1 | 11/2001 | Levinson et al. |
| 2001/0041909 A1 | 11/2001 | Tsugita et al. |
| 2001/0044632 A1 | 11/2001 | Daniel et al. |
| 2001/0044634 A1 | 11/2001 | Don Michael et al. |
| 2001/0053921 A1 | 12/2001 | Jang |
| 2002/0002384 A1 | 1/2002 | Gilson et al. |
| 2002/0004667 A1 | 1/2002 | Adams et al. |
| 2002/0016564 A1 | 2/2002 | Courtney et al. |
| 2002/0016609 A1 | 2/2002 | Wensel et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0026212 A1 | 2/2002 | Wholey et al. |
| 2002/0026213 A1 | 2/2002 | Gilson et al. |
| 2002/0032460 A1 | 3/2002 | Kusleika et al. |
| 2002/0032461 A1 | 3/2002 | Marshall |
| 2002/0042626 A1 | 4/2002 | Hanson et al. |
| 2002/0042627 A1 | 4/2002 | Brady et al. |
| 2002/0045915 A1 | 4/2002 | Balceta et al. |
| 2002/0045916 A1 | 4/2002 | Gray et al. |
| 2002/0045918 A1 | 4/2002 | Suon et al. |
| 2002/0049452 A1 | 4/2002 | Kurz et al. |
| 2002/0049468 A1 | 4/2002 | Streeter et al. |
| 2002/0052627 A1 | 5/2002 | Boylan et al. |
| 2002/0058904 A1 | 5/2002 | Boock et al. |
| 2002/0058911 A1 | 5/2002 | Gilson et al. |
| 2002/0058963 A1 | 5/2002 | Vale et al. |
| 2002/0058964 A1 | 5/2002 | Addis |
| 2002/0062133 A1 | 5/2002 | Gilson et al. |
| 2002/0062134 A1 | 5/2002 | Barbut et al. |
| 2002/0062135 A1 | 5/2002 | Mazzocchi et al. |
| 2002/0065507 A1 | 5/2002 | Zadno-Azizi |
| 2002/0068954 A1 | 6/2002 | Foster |
| 2002/0068955 A1 | 6/2002 | Khosravi |
| 2002/0072764 A1 | 6/2002 | Sepetka et al. |
| 2002/0072765 A1 | 6/2002 | Mazzocchi et al. |
| 2002/0077596 A1 | 6/2002 | McKenzie et al. |
| 2002/0082558 A1 | 6/2002 | Samson et al. |
| 2002/0082639 A1 | 6/2002 | Broome et al. |
| 2002/0087187 A1 | 7/2002 | Mazzocchi et al. |

| | | |
|---|---|---|
| 2002/0090389 A1 | 7/2002 | Humes et al. |
| 2002/0091407 A1 | 7/2002 | Zadno-Azizi et al. |
| 2002/0091408 A1 | 7/2002 | Sutton et al. |
| 2002/0091409 A1 | 7/2002 | Sutton et al. |
| 2002/0095170 A1 | 7/2002 | Krolik et al. |
| 2002/0095171 A1 | 7/2002 | Belef |
| 2002/0095172 A1 | 7/2002 | Mazzocchi et al. |
| 2002/0095173 A1 | 7/2002 | Mazzocchi et al. |
| 2002/0095174 A1 | 7/2002 | Tsugita et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111647 A1 | 8/2002 | Khairkhahan et al. |
| 2002/0111648 A1 | 8/2002 | Kusleika et al. |
| 2002/0111649 A1 | 8/2002 | Russo et al. |
| 2002/0116024 A1 | 8/2002 | Goldberg et al. |
| 2002/0120226 A1 | 8/2002 | Beck |
| 2002/0120286 A1 | 8/2002 | DoBrava et al. |
| 2002/0120287 A1 | 8/2002 | Huter |
| 2002/0123720 A1 | 9/2002 | Kusleika et al. |
| 2002/0123755 A1 | 9/2002 | Lowe et al. |
| 2002/0123759 A1 | 9/2002 | Amplatz |
| 2002/0123766 A1 | 9/2002 | Seguin et al. |
| 2002/0128679 A1 | 9/2002 | Turovskiy et al. |
| 2002/0128680 A1 | 9/2002 | Pavlovic |
| 2002/0128681 A1 | 9/2002 | Broome et al. |
| 2002/0133191 A1 | 9/2002 | Khosravi et al. |
| 2002/0133192 A1 | 9/2002 | Kusleika et al. |
| 2002/0138094 A1 | 9/2002 | Borillo et al. |
| 2002/0138095 A1 | 9/2002 | Mazzocchi et al. |
| 2002/0138096 A1 | 9/2002 | Hieshima |
| 2002/0138097 A1 | 9/2002 | Ostrovsky et al. |
| 2002/0143360 A1 | 10/2002 | Douk et al. |
| 2002/0143361 A1 | 10/2002 | Douk et al. |
| 2002/0143362 A1 | 10/2002 | Macoviak et al. |
| 2002/0151927 A1 | 10/2002 | Douk et al. |
| 2002/0151928 A1 | 10/2002 | Leslie et al. |
| 2002/0156520 A1 | 10/2002 | Boylan et al. |
| 2002/0161389 A1 | 10/2002 | Boyle et al. |
| 2002/0161390 A1 | 10/2002 | Mouw |
| 2002/0161391 A1 | 10/2002 | Murphy et al. |
| 2002/0161392 A1 | 10/2002 | Dubrul |
| 2002/0161393 A1 | 10/2002 | Demond et al. |
| 2002/0161394 A1 | 10/2002 | Macoviak et al. |
| 2002/0161395 A1 | 10/2002 | Douk et al. |
| 2002/0161396 A1 | 10/2002 | Jang et al. |
| 2002/0165557 A1 | 11/2002 | McAlister |
| 2002/0165573 A1 | 11/2002 | Barbut |
| 2002/0165576 A1 | 11/2002 | Boyle et al. |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173819 A1 | 11/2002 | Leeflang et al. |
| 2002/0177872 A1 | 11/2002 | Papp et al. |
| 2002/0183781 A1 | 12/2002 | Casey et al. |
| 2002/0183782 A1 | 12/2002 | Tsugita et al. |
| 2002/0183783 A1 | 12/2002 | Shadduck |
| 2002/0188313 A1 | 12/2002 | Johnson et al. |
| 2002/0188314 A1 | 12/2002 | Anderson et al. |
| 2002/0193824 A1 | 12/2002 | Boylan et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2002/0198561 A1 | 12/2002 | Amplatz |
| 2003/0004536 A1 | 1/2003 | Boylan et al. |
| 2003/0004538 A1 | 1/2003 | Secrest et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0004542 A1 | 1/2003 | Wensel et al. |
| 2003/0009146 A1 | 1/2003 | Muni et al. |
| 2003/0009189 A1 | 1/2003 | Gilson et al. |
| 2003/0009190 A1 | 1/2003 | Kletschka et al. |
| 2003/0009191 A1 | 1/2003 | Wensel et al. |
| 2003/0014072 A1 | 1/2003 | Wensel et al. |
| 2003/0018354 A1 | 1/2003 | Roth et al. |
| 2003/0018355 A1 | 1/2003 | Goto et al. |
| 2003/0023263 A1 | 1/2003 | Krolik et al. |
| 2003/0023264 A1 | 1/2003 | Dieck et al. |
| 2003/0023265 A1 | 1/2003 | Forber |
| 2003/0032976 A1 | 2/2003 | Boucek |
| 2003/0032977 A1 | 2/2003 | Brady |
| 2003/0040772 A1 | 2/2003 | Hyodoh et al. |
| 2003/0045897 A1 | 3/2003 | Huter et al. |
| 2003/0045898 A1* | 3/2003 | Harrison et al. ............. 606/200 |
| 2003/0050662 A1 | 3/2003 | Don Michael |
| 2003/0055452 A1 | 3/2003 | Joergensen et al. |
| 2003/0055480 A1 | 3/2003 | Fischell et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0065355 A1 | 4/2003 | Weber |
| 2003/0065356 A1 | 4/2003 | Tsugita et al. |
| 2003/0069596 A1 | 4/2003 | Eskuri |
| 2003/0073979 A1 | 4/2003 | Naimark et al. |
| 2003/0074019 A1 | 4/2003 | Gray et al. |
| 2003/0078614 A1 | 4/2003 | Salahieh et al. |
| 2003/0083692 A1 | 5/2003 | Vrba et al. |
| 2003/0083693 A1 | 5/2003 | Daniel et al. |
| 2003/0088211 A1 | 5/2003 | Anderson et al. |
| 2003/0088266 A1 | 5/2003 | Bowlin |
| 2003/0093110 A1 | 5/2003 | Vale |
| 2003/0093112 A1 | 5/2003 | Addis |
| 2003/0097094 A1 | 5/2003 | Ouriel et al. |
| 2003/0097145 A1 | 5/2003 | Goldberg et al. |
| 2003/0100917 A1 | 5/2003 | Boyle et al. |
| 2003/0100918 A1 | 5/2003 | Duane |
| 2003/0100919 A1 | 5/2003 | Hopkins et al. |
| 2003/0105472 A1 | 6/2003 | McAlister |
| 2003/0105484 A1 | 6/2003 | Boyle et al. |
| 2003/0105486 A1 | 6/2003 | Murphy et al. |
| 2003/0109824 A1 | 6/2003 | Anderson et al. |
| 2003/0109897 A1 | 6/2003 | Walak et al. |
| 2003/0114879 A1 | 6/2003 | Euteneuer et al. |
| 2003/0114880 A1 | 6/2003 | Hansen et al. |
| 2003/0120303 A1 | 6/2003 | Boyle et al. |
| 2003/0120304 A1 | 6/2003 | Kaganov et al. |
| 2003/0125764 A1 | 7/2003 | Brady et al. |
| 2003/0125765 A1 | 7/2003 | Blackledge et al. |
| 2003/0130680 A1 | 7/2003 | Russell |
| 2003/0130681 A1 | 7/2003 | Ungs |
| 2003/0130682 A1 | 7/2003 | Broome et al. |
| 2003/0130684 A1 | 7/2003 | Brady et al. |
| 2003/0130685 A1 | 7/2003 | Daniel et al. |
| 2003/0130686 A1 | 7/2003 | Daniel et al. |
| 2003/0130687 A1 | 7/2003 | Daniel et al. |
| 2003/0130688 A1 | 7/2003 | Daniel et al. |
| 2003/0135232 A1 | 7/2003 | Douk et al. |
| 2003/0135233 A1 | 7/2003 | Bates et al. |
| 2003/0139764 A1 | 7/2003 | Levinson et al. |
| 2003/0139765 A1 | 7/2003 | Patel et al. |
| 2003/0144685 A1 | 7/2003 | Boyle et al. |
| 2003/0144686 A1 | 7/2003 | Martinez et al. |
| 2003/0144687 A1 | 7/2003 | Brady et al. |
| 2003/0144688 A1 | 7/2003 | Brady et al. |
| 2003/0144689 A1 | 7/2003 | Brady et al. |
| 2003/0150821 A1 | 8/2003 | Bates et al. |
| 2003/0153935 A1 | 8/2003 | Mialhe |
| 2003/0153942 A1 | 8/2003 | Wang et al. |
| 2003/0153943 A1 | 8/2003 | Michael et al. |
| 2003/0153944 A1 | 8/2003 | Phung et al. |
| 2003/0153945 A1 | 8/2003 | Patel et al. |
| 2003/0158518 A1 | 8/2003 | Schonholz et al. |
| 2003/0158574 A1 | 8/2003 | Esch et al. |
| 2003/0158575 A1 | 8/2003 | Boylan et al. |

| | | |
|---|---|---|
| 2003/0163158 A1 | 8/2003 | White |
| 2003/0163159 A1 | 8/2003 | Patel et al. |
| 2003/0167068 A1 | 9/2003 | Amplatz |
| 2003/0167069 A1 | 9/2003 | Gonzales et al. |
| 2003/0171769 A1 | 9/2003 | Barbut |
| 2003/0171770 A1 | 9/2003 | Kusleika et al. |
| 2003/0171771 A1 | 9/2003 | Anderson et al. |
| 2003/0171772 A1 | 9/2003 | Amplatz |
| 2003/0171803 A1 | 9/2003 | Shimon |
| 2003/0176884 A1 | 9/2003 | Berrada et al. |
| 2003/0176885 A1 | 9/2003 | Broome et al. |
| 2003/0176886 A1 | 9/2003 | Wholey et al. |
| 2003/0176887 A1 | 9/2003 | Petersen |
| 2003/0176888 A1 | 9/2003 | O'Connell |
| 2003/0176889 A1 | 9/2003 | Boyle et al. |
| 2003/0181942 A1 | 9/2003 | Sutton et al. |
| 2003/0181943 A1 | 9/2003 | Daniel et al. |
| 2003/0717769 | 9/2003 | Barbut |
| 2003/0187474 A1 | 10/2003 | Keegan et al. |
| 2003/0187475 A1 | 10/2003 | Tsugita et al. |
| 2003/0187495 A1 | 10/2003 | Cully et al. |
| 2003/0191492 A1 | 10/2003 | Gellman et al. |
| 2003/0191493 A1 | 10/2003 | Epstein et al. |
| 2003/0195554 A1 | 10/2003 | Shen et al. |
| 2003/0195555 A1 | 10/2003 | Khairkhahan et al. |
| 2003/0199819 A1 | 10/2003 | Beck |
| 2003/0199917 A1 | 10/2003 | Knudson et al. |
| 2003/0199918 A1 | 10/2003 | Patel et al. |
| 2003/0199919 A1 | 10/2003 | Palmer et al. |
| 2003/0199920 A1 | 10/2003 | Boylan et al. |
| 2003/0199921 A1 | 10/2003 | Palmer et al. |
| 2003/0204168 A1 | 10/2003 | Bosma et al. |
| 2003/0204202 A1 | 10/2003 | Palmer et al. |
| 2003/0204203 A1 | 10/2003 | Khairkhahan et al. |
| 2003/0208222 A1 | 11/2003 | Zadno-Azizi |
| 2003/0208224 A1 | 11/2003 | Broome |
| 2003/0208225 A1 | 11/2003 | Goll et al. |
| 2003/0208226 A1 | 11/2003 | Bruckheimer et al. |
| 2003/0208227 A1 | 11/2003 | Thomas |
| 2003/0208228 A1 | 11/2003 | Gilson et al. |
| 2003/0208229 A1 | 11/2003 | Kletschka |
| 2003/0208253 A1 | 11/2003 | Beyer et al. |
| 2003/0212428 A1 | 11/2003 | Richter |
| 2003/0212429 A1 | 11/2003 | Keegan et al. |
| 2003/0212432 A1 | 11/2003 | Khairkhahan et al. |
| 2003/0212433 A1 | 11/2003 | Ambrisco et al. |
| 2003/0216774 A1 | 11/2003 | Larson |
| 2003/0220665 A1 | 11/2003 | Eskuri et al. |
| 2003/0220667 A1 | 11/2003 | Van der Burg et al. |
| 2003/0225435 A1 | 12/2003 | Huter et al. |
| 2003/0229374 A1 | 12/2003 | Brady et al. |
| 2003/0233117 A1 | 12/2003 | Adams et al. |
| 2004/0006364 A1 | 1/2004 | Ladd |
| 2004/0006370 A1 | 1/2004 | Tsugita |
| 2004/0039412 A1 | 2/2004 | Isshiki et al. |
| 2004/0059372 A1 | 3/2004 | Tsugita |
| 2004/0064067 A1 | 4/2004 | Ward |
| 2004/0068271 A1 | 4/2004 | McAlister |
| 2004/0078044 A1 | 4/2004 | Kear et al. |
| 2004/0082962 A1 | 4/2004 | Demarais et al. |
| 2004/0093016 A1 | 5/2004 | Root et al. |
| 2004/0098022 A1 | 5/2004 | Barone |
| 2004/0098033 A1 | 5/2004 | Leeflang et al. |
| 2004/0098112 A1 | 5/2004 | DiMatteo et al. |
| 2004/0106944 A1 | 6/2004 | Daniel et al. |
| 2004/0116831 A1 | 6/2004 | Vrba |
| 2004/0133232 A1 | 7/2004 | Rosenbluth et al. |
| 2004/0158278 A1 | 8/2004 | Becker et al. |
| 2004/0164030 A1 | 8/2004 | Lowe et al. |
| 2004/0167567 A1 | 8/2004 | Cano et al. |
| 2004/0176794 A1 | 9/2004 | Khosravi |
| 2004/0176833 A1 | 9/2004 | Pavcnik et al. |
| 2004/0236369 A1 | 11/2004 | Dubrul |
| 2005/0038468 A1 * | 2/2005 | Panetta et al. ............... 606/200 |
| 2006/0100544 A1 | 5/2006 | Ayala et al. |
| 2006/0100545 A1 | 5/2006 | Ayala et al. |
| 2006/0287701 A1 * | 12/2006 | Pal ............................ 623/1.11 |

FOREIGN PATENT DOCUMENTS

WO    WO 99/44510    9/1999

* cited by examiner

Fig. 8

EMBOLIC PROTECTION DEVICE HAVING A RETICULATED BODY WITH STAGGERED STRUTS

CROSS-REFERENCE TO RELATED APPLICATION

This application claims the benefit of U.S. Provisional Application No. 60/692,313, filed on Jun. 20, 2005, entitled "Embolic Protection Device Having A Reticulated Body With Staggered Struts", the entire contents of which are incorporated herein by reference.

BACKGROUND OF THE INVENTION

The present invention relates to medical devices. More particularly, the present invention relates to embolic protection devices and methods for capturing emboli within a body vessel.

Embolic protection to capture emboli within the vasculature is a growing concern in the medical industry. Currently, there are a number of treatments for embolic protection to prevent emboli and blood clots from traveling within the vasculature to create undesirable medical conditions, e.g., ischemic stroke, brain aneurysm, pulmonary embolism. For example, vena cava filters are more commonly being used for trapping blood clots and emboli in the vena cava filter to prevent pulmonary embolism. Also, anti-platelet agents and anticoagulants may be used to breakdown blood clots. Moreover, snares and baskets (e.g., stone retrieval baskets) are more commonly used for retrieving urinary calculi. Additionally, occlusion coils are commonly used to occlude aneurysms and accumulate thrombi in a body vessel.

Treatments for a stenotic lesion provide a potential in releasing blood clots and other thrombi plaque in the vasculature of the patient. One example is the treatment for a carotid artery stenosis. Generally, carotid artery stenosis is the narrowing of the carotid arteries, the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation process is called atherosclerosis.

Depending on the degree of stenosis and the patient's overall condition, carotid artery stenosis has been treated with surgery. The procedure (with its inherent risks) is called carotid endarterectomy, which removes the plaque from the arterial walls. Carotid endarterectomy has proven to benefit patients with arteries substantially narrowed, e.g., by about 70% or more. For people with less narrowed arteries, e.g., less than about 50%, an anti-clotting drug may be prescribed to reduce the risk of ischemic stroke. Examples of these drugs are anti-platelet agents and anticoagulants.

Carotid angioplasty is a more recently developed treatment for carotid artery stenosis. This treatment uses balloons and/or stents to open a narrowed artery. Carotid angioplasty is a procedure that can be performed via a standard percutaneous transfemoral approach with the patient anesthetized using light intravenous sedation. At the stenosis area, an angioplasty balloon is delivered to predilate the stenosis in preparation for stent placement. The balloon is then removed and exchanged via catheter for a stent delivery device. Once in position, a stent is deployed across the stenotic area. If needed, an additional balloon can be placed inside the deployed stent for post-dilation to make sure the struts of the stent are pressed firmly against the inner surface of the vessel wall.

During the stenosis procedure however, there is a risk of such blood clots and thrombi being undesirably released into the blood flow within the vasculature. Embolic or distal protection devices have been implemented to capture emboli from a stenotic lesion undergoing angioplasty. However, many current embolic protection devices restrict flow when deployed within the vasculature of the patient. Moreover, many embolic protection devices are relatively difficult to collapse and retrieve after the need for such device in the vasculature passes.

Thus, there is a need to provide an improved device and method for distally protecting and capturing emboli within a body lumen during a stenosis procedure.

BRIEF SUMMARY OF THE INVENTION

The present invention generally provides an embolic protection device that minimizes restricted flow when deployed within the vasculature of a patient and that is relatively easy to retrieve.

In one embodiment, the present invention provides an embolic protection device for capturing emboli during treatment of a stenotic lesion in a body vessel. The device comprises a basket and a filter connected to the basket. In this embodiment, the basket has a deployed state and an undeployed state. The basket includes a reticulated body having an outer diameter. The reticulated body includes a plurality of struts connected together in a singly staggered configuration distally along a longitudinal axis to a distal end. The plurality of struts of the reticulated body is configured to fold along the longitudinal axis. The basket further has a proximal stem proximally extending from the body. The filter portion has a lip attached to the distal end defining an opening of the filter portion when the basket is in the deployed state for capturing emboli. The filter portion extends from the lip to a filter end.

In another embodiment, the present invention provides an embolic protection assembly for capturing emboli during treatment of a stenotic lesion in a body vessel. The assembly comprises a balloon catheter having a tubular body portion and an expandable balloon attached to and in fluid communication with the tubular body portion for angioplasty at the stenotic lesion. The expandable balloon has distal and proximal portions. The assembly further comprises an embolic protection device coaxially disposed within the balloon catheter during treatment of the stenotic lesion in the body vessel. The device comprises the basket and the filter portion.

In another example, the present invention provides a method for embolic protection during treatment of a stenotic lesion in a body vessel. The method comprises percutaneously introducing a balloon catheter in the body vessel. The balloon catheter has a tubular body portion and an expandable balloon attached to and in fluid communication with the tubular body portion for angioplasty at the stenotic lesion. The method further comprises disposing the embolic protection device in an undeployed state coaxially with the balloon catheter. The method further comprises deploying the device in an deployed state downstream from the stenotic lesion to capture emboli during treatment of the stenotic lesion.

Further objects, features, and advantages of the present invention will become apparent from consideration of the

BRIEF DESCRIPTION OF THE DRAWINGS

FIG. 6b is an exploded side view of the assembly in FIG. 6a;

DETAILED DESCRIPTION OF THE INVENTION

The present invention generally provides an embolic protection device that minimizes restricted flow when deployed within the vasculature of a patient and that is relatively easy to retrieve after the risk of releasing blood clots and thrombi within the vasculature has passed. Embodiments of the present invention generally provide an embolic protection device comprising a basket having a reticulated body including a plurality of struts connected together in a singly staggered configuration distally along a longitudinal axis to an open distal end. The singly staggered configuration allows for relatively easy retrieval of the device. Moreover, the basket extends along the longitudinal axis having a substantially constant outer diameter to minimize restricted flow when deployed within the vasculature of a patient.

Figure 1:
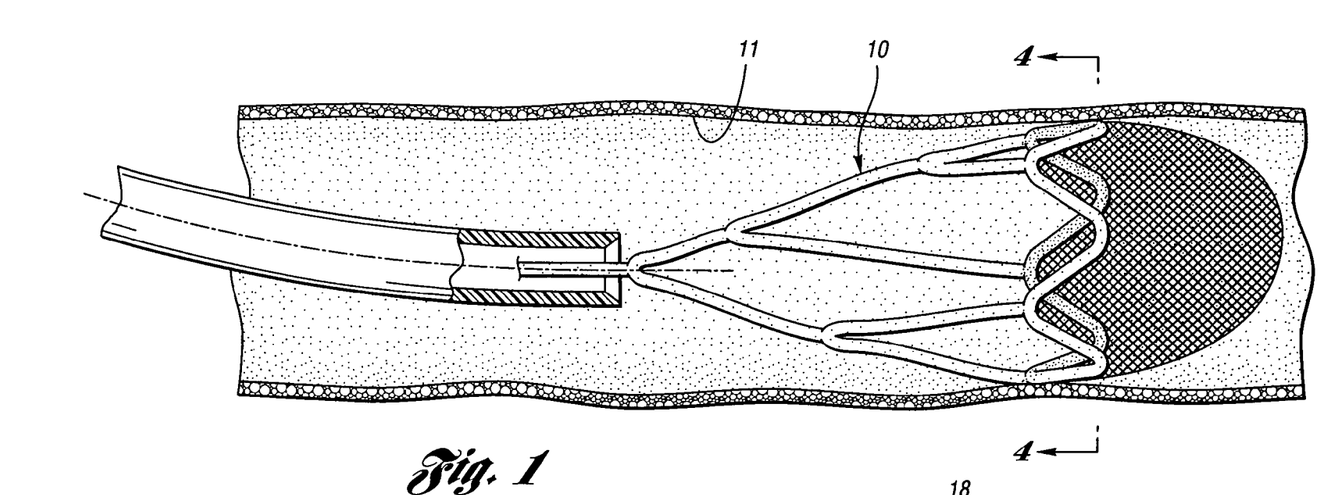
FIG. 1 is an environment view of an embolic protection device in accordance with one embodiment of the present invention.
Figure 2:
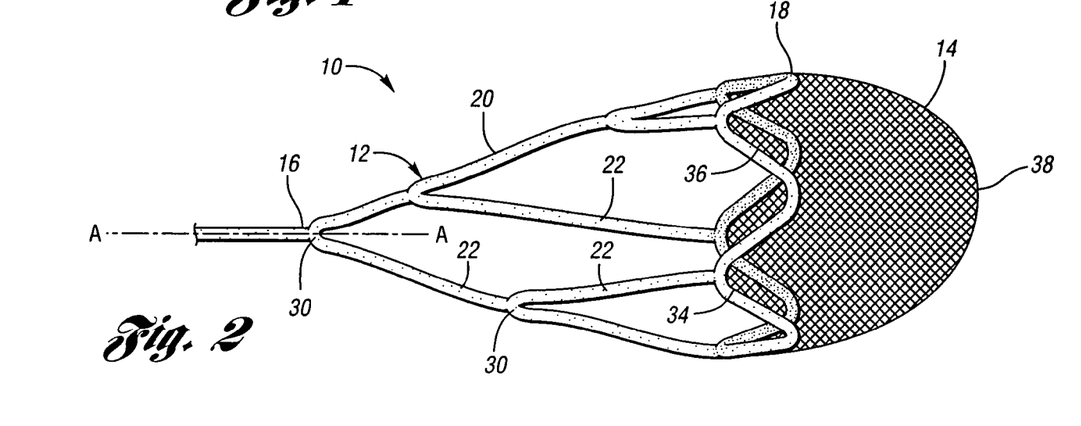
FIG. 2 is a perspective view of the emboli protection device of FIG. 1.

FIG. 1 illustrates an embolic protection device 10 for capturing emboli during treatment of a stenotic lesion in a body vessel 11 in accordance with one embodiment of the present invention. As shown in FIGS. 1 and 2, the device 10 comprises a basket 12 and a filter portion 14 attached to the basket 12 for capturing emboli in the body vessel 11. The basket 12 extends from an open proximal end 16 and an open distal end 18, and is configured to have an expanded state and a collapsed state.

In this embodiment, the basket 12 includes a reticulated body 20 extending along an outer diameter when in the expanded state. The reticulated body 20 includes a plurality of struts 22 distally connected together in a singly staggered configuration relative to a longitudinal axis A of the basket 12. As shown, the singly staggered configuration of the plurality of struts 22 distally extends from a proximal portion 24 of the reticulated body 20 along the longitudinal axis A to a distal portion 26 thereof. In the expanded state, each of the struts 22 of the reticulated body 20 is configured to fold singly in pairs along the longitudinal axis A to the collapsed state. As will be described in greater detail below, the singly staggered configuration allows the device 10 to be relatively easily collapsed and retrieved when deployed within the vasculature of a patient.

Figure 3:
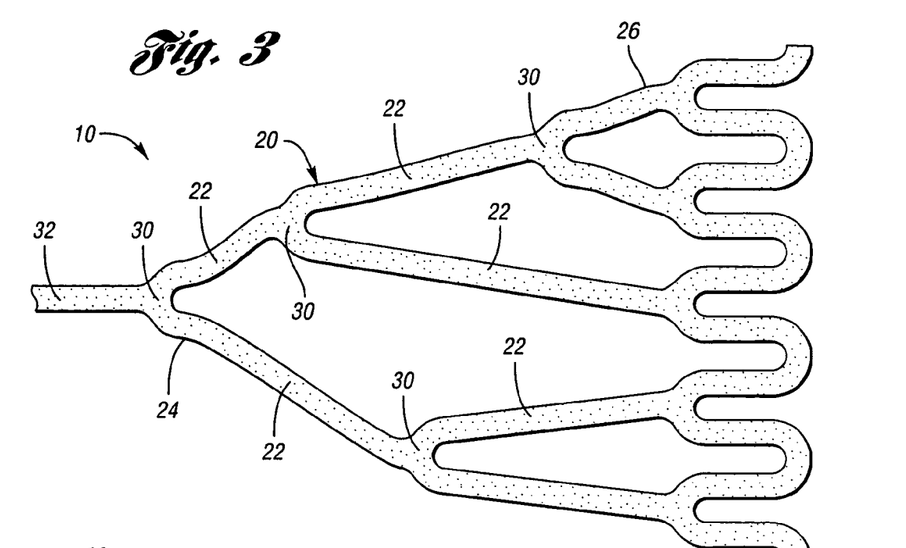
FIG. 3 is a plan view of the embolic protection device of FIG. 1.

As shown in FIGS. 2 and 3, the reticulated body 20 is formed so that each strut 22 is singly connected to another strut 22 in pairs relative to the longitudinal axis of the basket 12. Preferably, the struts 22 are connected together at pivotal joints 30 along the reticulated body 20. In this embodiment, one pair of struts 22 is connected at one pivotal joint 30. Each of the pivotal joints 30 is configured to allow a pair of struts 22 to singly fold distally along the longitudinal axis. As shown, a pair of struts 22 distally extends from a single pivotal joint 30 at the proximal stem 32. In this embodiment, two struts 22 are disposed on and extend from the proximal stem 32 and up to ten struts 22 may be formed at the distal portion 26 of the basket 12. When each of the pairs of struts 22 is folded at the pivotal joints 30, the reticulated body 20 is collapsed to its collapsed state for delivery or retrieval of the device 10. This feature allows a catheter to circumferentially ride over each pivotal joint 30 for relatively easy collapse and retrieval of the device 10.

Figure 4:
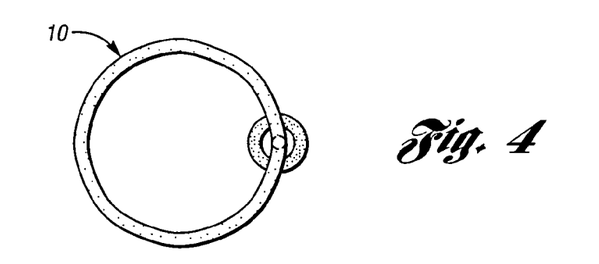
FIG. 4 is an end view of the embolic protection device in FIG. 1.

The reticulated body 20 distally extends from the proximal portion 24 to the distal portion 26 along the outer diameter. Preferably, the reticulated body 20 extends substantially constantly along the outer diameter when in the expanded state. As shown in FIGS. 3 and 4, the reticulated body 20 extends along the outer diameter and maintains substantially the same or constant diameter therealong from the proximal portion 24 to the distal portion 26 of the reticulated body 20. In the expanded state, the basket 12 avoids placement at or near the center of the body vessel in which it is deployed. Thus, this feature lessens restricted blood flow when the device 10 is deployed within the vasculature of a patient.

Preferably, the number of struts 22 and pivotal joints 30 on the reticulated body 20 distally increases in a singly staggered configuration along the longitudinal axis to the open distal end. As shown, struts 22 at the distal portion 26 of the reticulated body 20 are connected together along the outer diameter, defining the open distal end 18 of the basket 12.

As mentioned above, FIG. 4 illustrates that the reticulated body 20 maintains a substantially constant outer diameter relative to the longitudinal axis. As shown, the outer diameter of the body is substantially constant and extends between the proximal end and distal end of the reticulated body 20. In this embodiment, the term "constant outer diameter" of the body or "substantially constant outer diameter" of the body means that the body extends along the longitudinal axis having about the same outer diameter. For instance, if the outer diameter of the body at the proximal portion 24 is about 5 millimeters (mm), then the outer diameter of the body along the remainder of the body is also about 5 mm.

Figure 5:
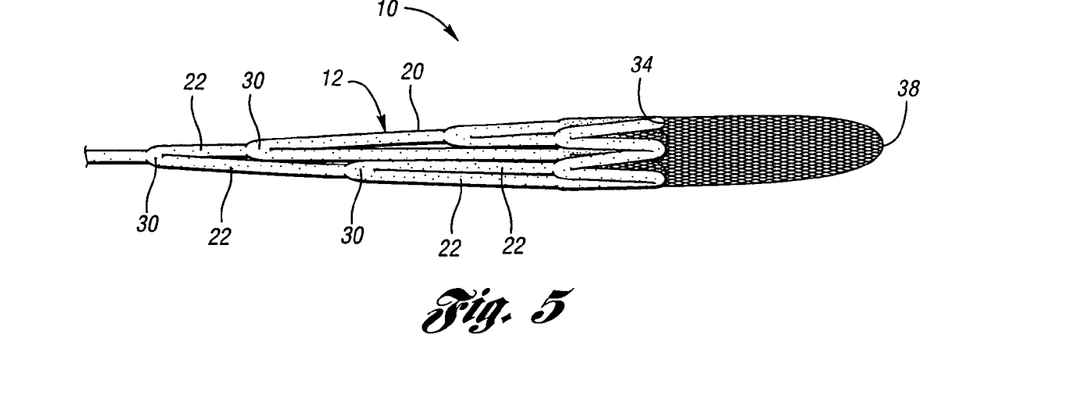
FIG. 5 is a side view of the embolic protection device in a collapsed configuration in accordance with one embodiment of the present invention.

FIG. 5 illustrates the device 10 in its collapsed or closed state in accordance with one embodiment of the present invention. As shown, the device 10 has a reduced diameter, occupying a cross-sectional profile less than the outer diameter of the device 10 in the expanded state. The pivotal joints 30 of the reticulated body 20 singly increase distally along the longitudinal axis of the device 10. As shown in FIG. 5, the reticulated body 20 in the collapsed state distally increases in width in a singly staggered configuration. For example, the reticulated body 20 in the collapsed configuration includes pairs of folded struts 22 singly staggered at their respective pivotal joints 30 which distally increase in number, thereby distally increasing the width as the body distally extends.

FIGS. 2-4 further depict the basket 12 having a proximal stem 32. As shown, the proximal stem 32 proximally extends from the proximal portion 24 of the basket 12 along the outer diameter thereof. Thus, the proximal stem 32 is positioned off-centered to allow maximum blood flow through the device 10 when deployed in a body vessel. The proximal stem 32 may proximally extend from the basket 12 and take on any suitable shape along the outer diameter of the basket 12. For example, the proximal stem 32 may take on a shape of an elongated member that may be disposed through a lumen of a balloon catheter 42 for placement of the embolic protection device 10 during treatment of a stenotic lesion. However, it is understood that the proximal stem 32 may take on other shapes without falling beyond the scope or spirit of the present invention.

As mentioned, the proximal stem 32 extends in alignment with the outer diameter of the basket 12 relative to a radial axis of the device 10. This allows for more effective filtering and lessens the risk of blood flow issues within the vasculature during angioplasty, while maintaining a relatively easy way for delivery and retrieval. However, the proximal stem 32 may be configured as desired to extend circumferentially within, in non-alignment with, the outer diameter of the device 10 relative to the radial axis.

The basket 12 may be comprised of any suitable material such as a superelastic material, stainless steel wire, cobalt-chromium-nickel-molybdenum-iron alloy, or cobalt-chrome alloy. It is understood that the basket 12 may be formed of any other suitable material that will result in a self-opening or self-expanding basket, such as shape memory alloys. Shape memory alloys have the desirable property of becoming rigid, that is, returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenic, such that material returns to its remembered state. The transition temperature is dependent on the relative proportions of the alloying elements Ni and Ti and the optional inclusion of alloying additives.

In one embodiment, the basket 12 is made from Nitinol with a transition temperature that is slightly below normal body temperature of humans, which is about 98.6° F. Thus, when the basket 12 is deployed in a body vessel and exposed to normal body temperature, the alloy of the basket 12 will transform to austenite, that is, the remembered state, which for one embodiment of the present invention is the expanded configuration when the basket 12 is deployed in the body vessel. To remove the basket 12, the basket 12 is cooled to transform the material to martensite which is more ductile than austenite, making the basket 12 more malleable. As such, the basket 12 can be more easily collapsed and pulled into a lumen of a catheter for removal.

In another embodiment, the basket 12 is made from Nitinol with a transition temperature that is above normal body temperature of humans, which is about 98.6° F. Thus, when the basket 12 is deployed in a body vessel and exposed to normal body temperature, the basket 12 is in the martensitic state so that the basket 12 is sufficiently ductile to bend or form into a desired shape, which for the present invention is an expanded configuration. To remove the basket 12, the basket 12 is heated to transform the alloy to austenite so that the basket 12 becomes rigid and returns to a remembered state, which for the basket 12 in a collapsed configuration.

As shown in FIG. 2, the filter portion 14 has a lip 34 attached to the distal end 18 of the reticulated body 20, defining an opening 36 of the filter portion 14 when the basket 12 is in the expanded state for capturing emboli. The lip 34 may be attached to the distal end by any suitable means including sonic bonding, thermal bonding, or adhesive bonding. As shown in FIGS. 2 and 5, the filter portion 14 extends from the lip 34 to a filter end 38 formed to be a proximally facing concave shape. The opening 36 of the filter portion 14 is configured to face toward the stenotic lesion.

The filter portion 14 may be comprised of any suitable material to be used for capturing emboli from the stenotic lesion during treatment thereof. In one embodiment, the filter portion 14 is made of connective tissue material for capturing emboli. In this embodiment, the connective tissue comprises extracellular matrix (ECM). As known, ECM is a complex structural entity surrounding and supporting cells that are found within mammalian tissues. More specifically, ECM comprises structural proteins (e.g., collagen and elastin), specialized protein (e.g., fibrillin, fibronectin, and laminin), and proteoglycans, a protein core to which are attached are long chains of repeating disaccharide units termed of glycosaminoglycans.

Most preferably, the extracellular matrix is comprised of small intestinal submucosa (SIS). As known, SIS is a resorbable, acellular, naturally occurring tissue matrix composed of ECM proteins and various growth factors. SIS is derived from the porcine jejunum and functions as a remodeling bioscaffold for tissue repair. SIS has characteristics of an ideal tissue engineered biomaterial and can act as a bioscaffold for remodeling of many body tissues including skin, body wall, musculoskeletal structure, urinary bladder, and also supports new blood vessel growth. In many aspects, SIS is used to induce site-specific remodeling of both organs and tissues depending on the site of implantation. In theory, host cells are stimulated to proliferate and differentiate into site-specific connective tissue structures, which have been shown to completely replace the SIS material in time.

In this embodiment, SIS is used to temporarily adhere the filter portion 14 to the walls of a body vessel in which the device 10 is deployed. SIS has a natural adherence or wettability to body fluids and connective cells comprising the connective tissue of a body vessel wall. Due to the temporary nature of the duration in which the device 10 is deployed in the body vessel, host cells of the wall will adhere to the filter portion 14 but not differentiate, allowing for retrieval of the device 10 from the body vessel.

In other embodiments, the filter portion 14 may also be made of a mesh/net cloth, nylon, polymeric material, Teflon, or woven mixtures thereof without falling beyond the scope or spirit of the present invention.

In use, the device 10 expands from the collapsed state to the expanded state, engaging the basket 12 with the body vessel. In turn, the lip 34 of the filter portion 14 expands to open the filter portion 14 for capturing emboli during treatment of the stenotic lesion. After the need for such device 10 in the vasculature passes, the device 10 may be retrieved. In one embodiment, a catheter may be used to move longitudinally about the basket 12 to singly collapse each pivotal joint 30 distally, thereby moving the basket 12 toward the collapsed state.

Figure 6A:
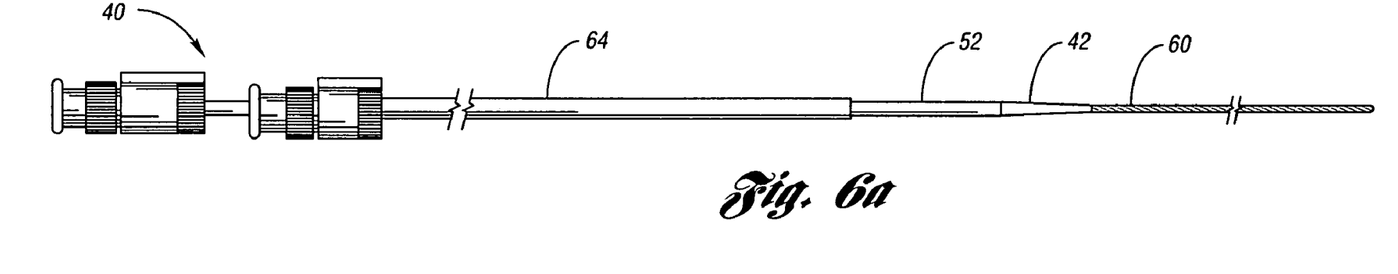
FIG. 6a is a side view of an embolic protection assembly for capturing emboli during treatment of a stenotic lesion in accordance with one embodiment of the present invention.
Figure 6B:
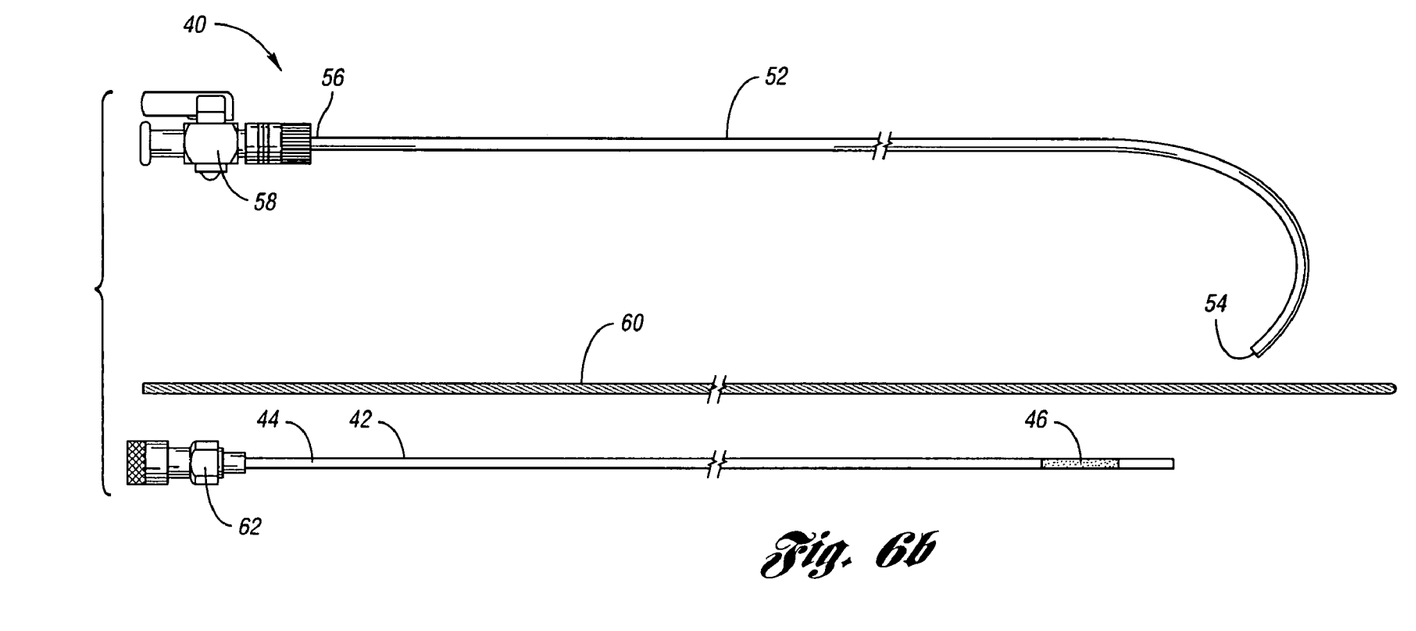

FIGS. 6a and 6b depict an embolic protection assembly 40 for capturing emboli during treatment of a stenotic lesion in a body vessel in accordance with another embodiment of the present invention. As shown, the assembly 40 comprises a balloon catheter 42 having a tubular body 44 and an expandable balloon 46 attached to and in fluid communication with the tubular body 44 for angioplasty at a stenotic lesion. In this embodiment, the assembly 40 comprises the embolic protection device mentioned above. The tubular body 44 is preferably made of soft flexible material such as silicon or any other suitable material. In this embodiment, the balloon catheter 42 includes an outer lumen 48 and an inner lumen 50. The outer lumen 48 is in fluid communication with the balloon 46 for inflating and deflating the balloon 46. The inner lumen 50 is formed therethrough for percutaneous guidance through the body vessel.

As shown, the assembly 40 further includes an inner catheter 52 having a distal end 54 through which the balloon catheter 42 is disposed for deployment in the body vessel. The inner catheter 52 is preferably made of a soft, flexible material such as silicon or any other suitable material. Generally, the inner catheter 52 further has a proximal end 56 and a plastic adaptor or hub 58 to receive the embolic protection device and balloon catheter 42 to be advanced therethrough. The size of the inner catheter 52 is based on the size of the body vessel in which it percutaneously inserts, and the size of the balloon catheter 42.

As shown, the assembly 40 may also include a wire guide 60 configured to be percutaneously inserted within the vasculature to guide the inner catheter 52 to a location adjacent a stenotic lesion. The wire guide 60 provides the inner catheter 52 (and balloon catheter 42) a path during insertion within the body vessel. The size of the wire guide 60 is based on the inside diameter of the inner catheter 52.

In one embodiment, the balloon catheter 42 has a proximal fluid hub 62 in fluid communication with the balloon 46 via the outer lumen 48 for fluid to be passed therethrough for inflation and deflation of the balloon 46 during treatment of the stenotic lesion.

As shown, the embolic protection device is coaxially disposed through the inner lumen 50 of the balloon catheter 42 prior to treatment of the stenotic lesion in the body vessel. The distal protection device is guided through the inner lumen 50 preferably from the hub 58 and distally beyond the balloon 46 of the balloon catheter 42, exiting from the distal end of the inner or balloon catheter 42 to a location within the vasculature downstream of the stenotic lesion.

In this embodiment, the apparatus further includes a polytetrafluoroethylene (PTFE) introducer sheath 64 for percutaneously introducing the wire guide 60 and the inner catheter 52 in a body vessel. Of course, any other suitable material may be used without falling beyond the scope or spirit of the present invention. The introducer sheath 64 may have any suitable size, e.g., between about three-french to eight-french. The introducer serves to allow the inner and balloon catheters 42 to be percutaneously inserted to a desired location in the body vessel. The introducer sheath 64 receives the inner catheter 52 and provides stability to the inner catheter at a desired location of the body vessel. For example, the introducer sheath 64 is held stationary within a common visceral artery, and adds stability to the inner catheter 52, as the inner catheter 52 is advanced through the introducer sheath 64 to a dilatation area in the vasculature.

When the distal end 54 of the inner catheter 52 is at a location downstream of the dilatation area in the body vessel, the balloon catheter 42 is inserted therethrough to the dilatation area. The device is then loaded at the proximal end of the balloon catheter 42 and is advanced through the inner lumen 50 thereof for deployment through its distal end. In this embodiment, the proximal stem is used to mechanically advance or push the device 10 through the catheter.

Figure 7:
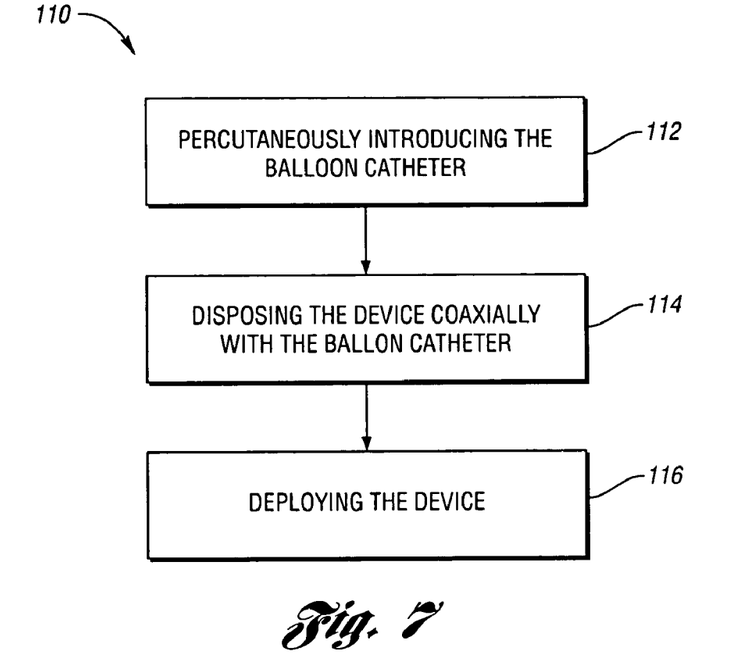
FIG. 7 is a flow chart of one method for embolic protection during treatment of a stenotic lesion in a body vessel.

FIG. 7 depicts a flow chart of one method 110 for embolic protection during treatment of stenotic lesion in a body vessel. The method 110 comprises percutaneously introducing the balloon catheter 42 in a body vessel in box 112, after the inner catheter is disposed to a dilatation area within the body vessel. The physician may use any suitable means of verifying the placement of the balloon catheter at a dilatation area, e.g., fluoroscopy.

In this example, the method further comprises disposing the embolic protection device in the collapsed state coaxially with the balloon catheter in box 114, once the balloon catheter is placed at the dilatation area. The method 110 further includes deploying the device in a deployed state downstream from the stenotic lesion to capture emboli during treatment of the stenotic lesion in box 116.

Figure 8:
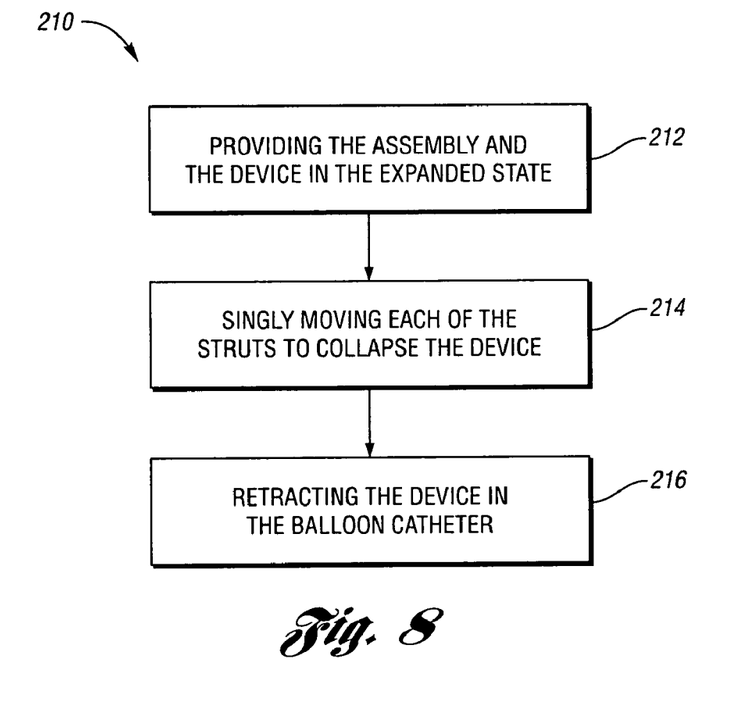
FIG. 8 is a flow chart of one method for retrieving an embolic protection device for post-treatment of a stenotic lesion in a body vessel.

In yet another example of the present invention, FIG. 8 depicts one method 210 of retrieving an embolic protection device for post-treatment of a stenotic lesion in a body vessel. The method comprises providing the embolic protection assembly having the embolic protection device in a deployed state within the body vessel in box 212. The method further comprises singly moving each of the struts about each pivotal joint to collapse the reticulated body in the undeployed state in box 214. The method further includes retracting the embolic protection device in the balloon catheter to retrieve the embolic protection device from the body vessel in box 216.

While the present invention has been described in terms of preferred embodiments, it will be understood, of course, that the invention is not limited thereto since modifications may be made to those skilled in the art, particularly in light of the foregoing teachings.

The invention claimed is:

1. An embolic protection device for capturing emboli during treatment of a stenotic lesion in a body vessel, the device comprising:
    a basket having a deployed state and an undeployed state, the basket including a reticulated body having an outer diameter, the reticulated body including a plurality of struts connected together in a singly staggered configuration relative to a longitudinal axis of the basket, the singly staggered configuration of the plurality of struts extending distally from a proximal end of the reticulated body along the longitudinal axis to a distal end, the plurality of struts being connected together at pivotal joints along the reticulated body, each pivotal joint connecting a pair of struts, wherein the number of pivotal joints singly increases distally along the longitudinal axis between the proximal and distal ends to define the singly staggered configuration of the plurality of struts, wherein the reticulated body in the undeployed state distally increases in width in the singly staggered configuration, the distal end defining the greatest width in the undeployed state, the pairs of struts connected by the pivotal joints being configured to singly fold distally along the longitudinal axis from the deployed state to the undeployed state, the basket having a proximal stem proximally extending from the body; and
    a filter portion having a lip attached to the distal end defining an opening of the filter portion when the basket is in the deployed state for capturing emboli, the filter portion extending from the lip to a filter end.

2. The device of claim 1 wherein the distal end distally extends from the reticulated body along the outer diameter.

3. The device of claim 1 wherein the number of struts on the reticulated body increases in a singly staggered configuration along the longitudinal axis of the reticulated body.

4. The device of claim 3 wherein the number of struts at the proximal stem of the body is one strut and the number of struts at the distal end is up to 10 struts.

5. The device of claim 1 wherein the outer diameter of the body is substantially constant and extends between the proximal stem and distal end of the reticulated body.

6. The device of claim 1 wherein the opening of the filter portion is configured to face toward the stenotic lesion in the body vessel proximal to the closed end thereof.

7. The device of claim 1 wherein the filter portion comprises a net material for capturing emboli from the stenotic lesion.

8. The device of claim 1 wherein the reticulated body is made of shape memory material configured to expand the reticulated body in the deployed state at a first temperature and collapse the reticulated body in the undeployed state at a second temperature.

* * * * *